US010112166B2

(12) United States Patent
Close et al.

(10) Patent No.: US 10,112,166 B2
(45) Date of Patent: Oct. 30, 2018

(54) METHOD FOR CAPTURING AND RECYCLING IRON CATALYST USED IN THE PRODUCTION OF HALOALKANE COMPOUNDS

(75) Inventors: Joshua Close, Blasdell, NY (US);
Haiyou Wang, Amherst, NY (US);
Hsueh Sung Tung, Getzville, NY (US);
Stephen A. Cottrell, Williamsville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 59 days.

(21) Appl. No.: 13/471,601

(22) Filed: May 15, 2012

(65) Prior Publication Data
US 2012/0305454 A1    Dec. 6, 2012

Related U.S. Application Data

(60) Provisional application No. 61/492,907, filed on Jun. 3, 2011.

(51) Int. Cl.
| | |
|---|---|
| *B03C 5/00* | (2006.01) |
| *B01J 8/10* | (2006.01) |
| *B01J 8/00* | (2006.01) |
| *C07C 17/275* | (2006.01) |
| *C07C 17/278* | (2006.01) |
| *B03C 1/033* | (2006.01) |
| *B01J 23/745* | (2006.01) |

(52) U.S. Cl.
CPC ............... *B01J 8/10* (2013.01); *B01J 8/005* (2013.01); *B01J 8/0075* (2013.01); *B03C 1/0335* (2013.01); *B03C 5/00* (2013.01); *C07C 17/275* (2013.01); *C07C 17/278* (2013.01); *B01J 23/745* (2013.01); *B03C 2201/02* (2013.01); *B03C 2201/18* (2013.01); *Y02P 20/584* (2015.11)

(58) Field of Classification Search
CPC ..................... B03C 2201/02; B03C 2201/18
USPC ........ 209/12.2, 38–40, 127.1–131, 212–232, 209/478–482, 695, 222, 223; 210/695, 210/222, 223
See application file for complete search history.

(56) References Cited

U.S. PATENT DOCUMENTS

| | | | | |
|---|---|---|---|---|
| 4,605,678 A | * | 8/1986 | Brennan et al. .............. | 518/700 |
| 5,902,914 A | | 5/1999 | Rygas et al. | |
| 6,187,978 B1 | | 2/2001 | Rygas et al. | |

(Continued)

FOREIGN PATENT DOCUMENTS

| | | |
|---|---|---|
| CN | 2535130 Y | 2/2003 |
| EP | 0014802 A1 | 9/1980 |

(Continued)

*Primary Examiner* — Jeremy R Severson

(57) ABSTRACT

Disclosed is a method for capturing and recycling iron catalyst used in the production of haloalkane compounds and more particularly, to an improved process for the manufacture of the compound 1,1,1,3,3-pentachloropropane (HCC-240fa), in which an electromagnetic separation unit (EMSU) is used to facilitate the reaction. When energized, the EMSU functions to remove all iron particles from the reactor effluent; when de-energized, the iron particles captured by the EMSU can be flushed back into the reactor for re-use in the continued production of HCC-240fa. The present invention is also useful in the manufacturing processes for other haloalkane compounds such as HCC-250 and HCC-360.

12 Claims, 1 Drawing Sheet

(56) References Cited

U.S. PATENT DOCUMENTS

| | | |
|---|---|---|
| 6,198,010 B1 | 3/2001 | Yoshikawa et al. |
| 6,235,951 B1 | 5/2001 | Sakyu et al. |
| 6,313,360 B1 * | 11/2001 | Wilson et al. ............... 570/257 |
| 6,500,993 B1 | 12/2002 | Mathieu et al. |
| 6,720,466 B2 | 4/2004 | Wilson et al. |
| 7,102,041 B2 | 9/2006 | Tung |
| 7,112,709 B2 | 9/2006 | Klausmeyer |
| 7,265,082 B2 | 9/2007 | Pham et al. |
| 8,052,875 B2 * | 11/2011 | Oder et al. ................... 210/695 |
| 2004/0225166 A1 | 11/2004 | Wilson et al. |
| 2005/0035030 A1 * | 2/2005 | Oder et al. ................... 209/232 |
| 2008/0091053 A1 | 4/2008 | Tung et al. |
| 2009/0065437 A1 * | 3/2009 | Mohedas .................... 210/695 |

FOREIGN PATENT DOCUMENTS

| | | |
|---|---|---|
| JP | H03-56153 A | 3/1991 |
| WO | 2003064052 A2 | 8/2003 |
| WO | 2008045910 A1 | 4/2008 |

\* cited by examiner

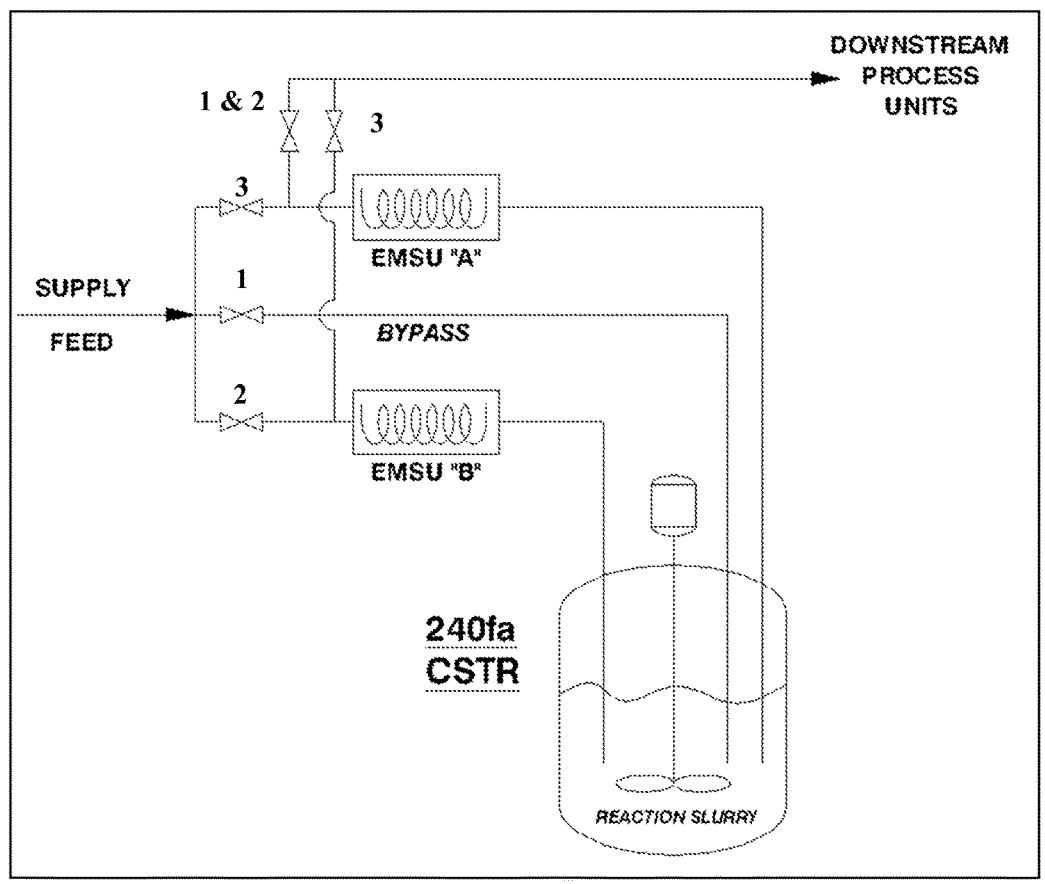

METHOD FOR CAPTURING AND RECYCLING IRON CATALYST USED IN THE PRODUCTION OF HALOALKANE COMPOUNDS

CROSS-REFERENCE TO RELATED APPLICATION

This application claims domestic priority to commonly owned, U.S. Provisional Patent Application Ser. No. 61/492,907, filed Jun. 3, 2011, the disclosure of which is hereby incorporated herein by reference.

FIELD OF THE INVENTION

The present invention relates to a process for the manufacture of haloalkane compounds, and more particularly, to an improved process for the manufacture of the compound 1,1,1,3,3-pentachloropropane (HCC-240fa). The present invention is also useful in the manufacturing processes for other haloalkane compounds such as HCC-250 and HCC-360.

BACKGROUND OF THE INVENTION

The compound 1,1,1,3,3-pentachloropropane (HCC-240fa) is a raw material for producing 1,1,1,3,3-pentafluoropropane (HFC-245fa), which is a non-ozone depleting chemical and can be used as blowing agent, energy transfer medium, and so on. Addition reactions for preparing useful haloalkanes, such as HCC-240fa, are known in the art. For example, U.S. Pat. No. 6,313,360 teaches a process for producing HCC-240fa by reacting carbon tetrachloride ($CCl_4$) and vinyl chloride (VCM) in the presence of a catalyst mixture comprising organophosphate, e.g., tributyl phosphate (TBP), metallic iron and ferric chloride under conditions sufficient to produce a product mixture containing HCC-240fa. The 240fa product is then recovered by separating it from reactants, catalyst and by-products. See also, U.S. Pat. Nos. 5,902,914, 6,187,978, 6,198,010, 6,235,951, 6,500,993, 6,720,466, 7,102,041, 7,112,709 and 7,265,082 and U.S. Patent Publication Nos. 2004/0225166 and 2008/0091053. The disclosures of all of these references are hereby incorporated herein by reference.

Iron powder is used as the primary catalyst during the synthesis of HCC-240fa via the coupling reaction between $CCl_4$ and VCM. The liquid medium, consisting of $CCl_4$, TBP, and 240fa, forms a slurry with the iron powder. As such, the reactor effluent will contain a substantial quantity of suspended solids which could potentially upset the mechanical and chemical operations of downstream units. Furthermore, as catalyst is removed from the effluent, the reactivity will suffer, increasing the required make-up of lost iron powder. Hence, there is a need for means by which iron catalyst can be captured and recycled back to reactor. The present invention provides a solution to this problem.

SUMMARY OF THE INVENTION

The present invention employs an electromagnetic separation unit (EMSU), configured to allow for the continuous removal of iron particles from reactor effluent and for the recycle of captured iron particles during the catalytic formation of haloalkane compounds from $CCl_4$.

In one embodiment, the present invention can be generally described as a method for capturing and recycling iron catalyst used in the production of 1,1,1,3,3-pentachloropropane, in which an electromagnetic separation unit (EMSU) is used to facilitate the reaction. When energized, the EMSU functions to remove all iron particles from the reactor effluent; when de-energized, the iron particles captured by the EMSU can be flushed back into the reactor for re-use.

Thus, one embodiment of the present invention is a method for capturing and recycling iron catalyst during in the production of 1,1,1,3,3-pentachloropropane, comprising the steps of:

(a) feeding $CCl_4$ and VCM into a reactor with a catalyst comprising iron powder and TBP to form HCC-240fa;

(b) removing the iron particles from the HCC-240fa reactor effluent by employing an energized electromagnetic separation unit (EMSU); and (c) denenergizing the EMSU and recycling the iron particles and returning the iron particles to the reactor for re-use in step (a).

The present invention is also useful in the iron catalyzed manufacturing processes for other haloalkane compounds such as HCC-250 and HCC-360:

(1) HCC-250 may be made from $CCl_4$ and ethylene as per the following reaction:

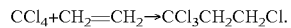

(2) HCC-360 may be made from $CCl_4$ and 2-chloropropene as per the following reaction:

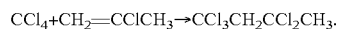

BRIEF DESCRIPTION OF THE DRAWING

The FIGURE shows the process setup for the continual removal and recycle of catalytic solids in the production of HCC-240fa and other haloalkane compounds, in a continuous stirred tank reactor (CSTR).

DETAILED DESCRIPTION OF THE INVENTION

Iron is widely used in many catalyst applications wherein its powder form is suspended in a liquid mixture which would be composed of chemical reactants. Often these slurries are processed continuously and may require careful management of the solids present. Sometimes downstream equipment (i.e., pumps, valves, piping) is unable to handle streams large amounts solid material. Furthermore, undesirable chemistries (separations, side reactions) may exist in the presence of iron. While iron powder is preferred, any iron object can be used, such as iron balls, iron wire, iron shavings, and the like.

Filters are often used and strategically placed to prevent downstream carry-over of solids. However, these filters generally need to be removed from service when they are saturated with iron. As a result, valuable catalyst may be lost and/or process downtime may exist as a result of clean and maintenance of these filters.

The present invention is designed to minimize iron carry-over and process downtime, during the iron catalyzed formation of haloalkane compounds from $CCl_4$, as well as to maximize catalyst retention in a process that employs suspensions of iron solids through the use of one or more electromagnetic separation units (EMSUs). Such devices are commercially available. One commercial manufacturer is Eriez of Erie, Pa.

More particularly, the present invention is designed to capture and recycle iron catalyst used in the production of 1,1,1,3,3-pentachloropropane, in which $CCl_4$ and VCM are continuously fed into the reactor at desired ratio and iron powder and the co-catalyst TBP can be added into reactor periodically or continuously. Additional co-catalysts useful herein are the following; tributylphosphate, triethylphosphate, trimethylphosphate, tripropylphosphate or any other trialkylphosphate compound, and mixtures of two or more of these.

The reaction of $CCl_4$ and VCM is preferably carried out at a residence time of from about 0.01 hours to about 24 hours, preferably from about 1 hour to about 12 hours. The reaction conditions are judicially selected for high VCM efficiency, high HCC-240fa yield, and low by-products production. While batch processing can be used for the reactions of the present invention, it is preferred that continuous manufacturing processing is used herein.

In a continuous operation, reactor contents are continually drawn through a tube immersed into the liquid slurry. As the slurry is removed from the reactor, the stream would be prepared by removing iron using an EMSU prior to downstream processing. Although this stream can be processed with a single EMSU, in a preferred embodiment, two (or more) tandem EMSUs are installed and operated in parallel, as shown in FIG. 1.

At start-up, valves 1 are opened allowing feed material to prime the 240fa reactor though the bypass and effluent to be directed through EMSU "A". Upon continuous operation, EMSU "A" will be energized. This energized EMSU accepts reactor effluent and operates to capture suspended iron particles. The liquid portion can then continue downstream free of iron. Once EMSU "A" becomes saturated with iron, valves 1 are closed and 3 are opened such that EMSU "B" can accept reactor effluent and begin removing iron.

While the EMSU "B" is operating, the saturated EMSU "A" is de-energized. Reactor supply can then be re-directed through the saturated EMSU "A" such that the iron catalyst is flushed back into the reactor. As such, a continuous process can be maintained by trading the tasks of each EMSU, either by opening valves 3 when EMSU "A" is saturated or valves 2 when EMSU "B" saturated, to prevent loss of iron to the downstream, maximize catalyst use, and mitigate process downtime.

After going through an EMSU where iron particles are trapped, the reactor effluent stream is flash-distilled to remove a "top" stream including unreacted $CCl_4$ and VCM (if any) feed materials and the HCC-240 reaction product, while the catalyst/co-catalyst mixture remains. The distillation may be performed in one or more distillation columns, which are well known in the art.

Preferably, the flash-distillation is conducted in two steps: first, flash-distillation is conducted at a temperature less than the reaction temperature under a pressure, preferably under vacuum, to remove any unreacted $CCl_4$ and/or VCM, followed by another vacuum flash-distillation at a lower pressure to remove the HCC-240fa reaction product. The "bottoms" stream is recycled back to the reactor. The distilled, unreacted $CCl_4$ and VCM may be recycled back to the reactor. Periodic purges may be applied to avoid accumulation of heavy by-products such as HCC-470 isomers in catalyst recycle stream.

In a later step of the process, the present invention provides for the purification of the crude product by distillation. Fractional vacuum distillation is carried out at about 5 to about 200 mm Hg and a temperature of about 50° C. to about 150° C. to recover the product. It has been discovered that when this purification step is carried out in the presence of a trialkyl phosphate such as tributyl phosphate or other metal chelating compound, the distillation yield of purified product is significantly improved.

While not wishing to be bound by any particular theory, it is believed that the tributylphosphate acts to prevent the decomposition of the HCC-240fa product. Thus, in a preferred embodiment, the purification step includes the addition of an amount of a metal chelating compound sufficient to improve the HCC-240fa product yield. Preferably, 5 weight percent of tributyl phosphate is used.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the production of 1,1,1,3,3-pentachloropropane (HCC-240fa) wherein carbon tetrachloride ($CCl_4$) and vinyl chloride (VCM) are reacted with a catalytic amount of iron powder and a co-catalyst selected from tributylphosphate, triethylphosphate, trimethylphosphate, tripropylphosphate, another trialkylphosphate compound, and mixtures of two or more of these;
   wherein the reaction of $CCl_4$ and VCM is carried out at a residence time of from about 0.01 hours to about 24 hours;
   wherein one or more electromagnetic separation units (EMSUs) are used to capture suspended iron powder particles from the reaction mixture, thereby producing an iron-free reactor effluent;
   wherein the iron-free reactor effluent is distilled to separate unreacted $CCl_4$ and/or VCM from the HCC-240 reaction product.

2. The process of claim 1, wherein the reaction residence time is from about 1 hour to about 12 hours.

3. The process of claim 1, wherein the distillation is a vacuum flash-distillation.

4. The process of claim 3, wherein the flash-distillation is conducted in two steps:
   first, vacuum flash-distillation is conducted to remove $CCl_4$ and/or VCM; and
   second, another vacuum flash-distillation is conducted at a lower pressure than that used in the first step, to remove the HCC-240fa reaction product.

5. The process of claim 4, wherein the second vacuum distillation is carried out at about 5 to about 200 mm Hg and a temperature of about 50° C. to about 150° C. to recover the HCC-240fa product.

6. The process of claim 5, wherein the second vacuum distillation is carried out in the presence of a trialkyl phosphate.

7. The process of claim 6, wherein the trialkyl phosphate is tributyl phosphate.

8. The process of claim 7, wherein 5 weight percent of tributyl phosphate is used.

9. The process of claim 1, wherein batch processing is used for the reaction.

10. The process of claim 1, wherein a continuous manufacturing process is used for the reaction.

11. The process of claim 1, wherein two or more tandem EMSUs are used.

12. In a process for the manufacture of the compound 1,1,1,3,3-pentachloropropane (HCC-240fa) comprising reacting carbon tetrachloride ($CCl_4$) and vinyl chloride (VCM) in the presence of a catalyst mixture comprising tributyl phosphate (TBP), metallic iron powder to produce a reaction product mixture containing HCC-240fa; and wherein the HCC-240fa product is recovered by separating it from the other reactants; the improvement comprising:

(a) continuously feeding $CCl_4$ and VCM into the reactor and adding iron powder and the co-catalyst TBP into reactor either periodically or continuously;

(b) conducting the reaction of the $CCl_4$ and VCM at a residence time of from about 1 hour to about 12 hours, thereby forming a reaction slurry of HCC-240fa and other reaction components;

(c) continuously withdrawing slurry from the reactor and passing the slurry through one or more electromagnetic separation units (EMSU) to remove the iron powder from the slurry, thereby producing an iron-free reactor effluent, and returning the iron powder to the reactor at step (a); and (d) separating the HCC-240fa from the slurry and returning the remaining contents of the slurry to the reactor at step (a).

* * * * *